United States Patent [19]

Huber et al.

[11] 4,042,689
[45] Aug. 16, 1977

[54] ALKYLATED ORGOTEIN

[75] Inventors: Wolfgang Huber, Atherton; Mark G. Saifer, Berkeley; Lewis D. Williams, Menlo Park, all of Calif.

[73] Assignee: Diagnostic Data, Inc., Mountain View, Calif.

[21] Appl. No.: 611,657

[22] Filed: Sept. 9, 1975

[51] Int. Cl.$^2$ .................... A61K 37/02; A61K 37/14; C07G 7/04
[52] U.S. Cl. ............................... 424/177; 260/112 R; 260/113; 260/115; 424/88; 424/287
[58] Field of Search ............... 260/112 R, 112 B, 113, 260/115; 424/12, 177, 287

[56] References Cited

U.S. PATENT DOCUMENTS

| 3,687,927 | 8/1972 | Huber | 424/112 R X |
|---|---|---|---|
| 3,758,682 | 9/1973 | Huber | 424/112 R X |

OTHER PUBLICATIONS

Stansell, J. Biol. Chem., vol. 240, 1965, pp. 4306–4311.
Hartz, J. Biol. Chem, vol. 244, 1969, pp. 4565–4572.
Carrico, J. Biol. Chem, vol. 244, 1969, pp. 6087–6093.
Cole, J. Biol. Chem, vol. 233, 1958, pp. 1359–1363.
Neurath, The Proteins, Acad. Press, vol. I, 2nd Ed., 1963, pp. 14, 15, 383, 406–412.

Primary Examiner—Albert T. Meyers
Assistant Examiner—A. P. Fagelson
Attorney, Agent, or Firm—Millen & White

[57] ABSTRACT

N-alkylated orgotein, like the native protein, possesses superoxide dismutase and anti-inflammatory activity.

15 Claims, No Drawings

ALKYLATED ORGOTEIN

BACKGROUND OF THE INVENTION

This invention relates to orgotein derivatives.

Orgotein is the non-proprietary name assigned by the United States Adopted Name Council to members of a family of water-soluble protein congeners in substantially pure, injectable form, i.e., substantially free from other proteins which are admixed or associated therewith in the sources thereof. U.S. Pat. No. 3,758,682 claims pharmaceutical compositions comprising orgotein.

The orgotein metalloproteins are members of a family of protein congeners having a characteristic combination of physical, chemical, biological and pharmacodynamic properties. Each of these congeners is characterized physically by being the isolated, substantially pure form of a globular, buffer and water-soluble protein having a highly compact native conformation which, although heat labile, is stable to heating for several minutes at 65° C. at pH 4–10. Chemically, each is characterized by containing all but 0–2 of the protein aminoacids, a small percentage of carbohydrate, no lipids, 0.1 to 1.0% metal content provided by one to 5 gram atoms per mole of one or more chelated divalent metals having an ionic radius of 0.60 to 1.00 A., and substantially no chelated monovalent metals or those that are cell poisons in the molecule.

The aminoacid composition of the orgotein congeners is remarkably consistent irrespective of the source from which it is isolated.

Table I lists the distribution of aminoacid residues, calculated for a molecular weight of 32,500 of several orgotein congeners.

In another composition aspect, this invention relates to pharmaceutical compositions comprising the novel alkylated orgoteins of this invention.

In a method of use aspect, this invention relates to the treatment of inflammatory conditions with a composition of this invention.

DETAILED DISCUSSION

The native orgotein protein possesses uniquely high superoxide dismutase activity. See McCord and Fridovich, J. Biol. Chem., b 244, 6,049 (1969); Keele, McCord and Fridovich, J. Biol. Chem., 245, 6,176 (1970); ibid., 246, 2,875 (1971). A substantial portion of this activity is retained upon alkylation of the lysine groups, e.g., to 20–100% of the native protein. The anti-inflammatory activity of native protein also is substantially unaffected by alkylation. Accordingly, the alkylated protein is useful in the same manner as the native protein for the treatment of inflammatory conditions in mammals and other animals as disclosed in U.S. Pat. No. 3,758,682, whose disclosure is incorporated by reference.

As stated above, orgotein congeners contain from 18–26 lysine groups. Since the orgotein molecule is made up of two identical peptide chains (sub-units), half of these lysine groups are in each chain, which are tightly but non-covalently bound together under moderate conditions of temperature and pH. Because of the spacial conformation of the orgotein molecule, usually the $\epsilon$-amino groups of a few lysines in each chain are not titratable with trinitrobenzenesulfonic acid (TNBS) and thus not readily accessible for alkylation. However, alkylation of the non-tritable lysine $\epsilon$-amino groups also appears possible employing a highly active alkylating agent, e.g., dimethyl sulfate at an alkaline pH. The ex-

TABLE I

AMINO ACID COMPOSITION OF SEVERAL ORGOTEIN CONGENERS
[Residues per mole, M.W. = 32,500]

| Aminoacids | Liver, Beef | Red Blood Cells (RBC) | | | | | | | | | | Range |
| --- | --- | --- | --- | --- | --- | --- | --- | --- | --- | --- | --- | --- |
| | | Beef | Sheep | Horse | Pork | Dog | Rabbit | Rat | Guinea Pig | Chicken | Human | |
| Alanine | 19 | 19 | 18 | 18 | 18 | 16 | 19 | 22 | 22 | 23 | 22 | 16–23 |
| Arginine | 8 | 8 | 10 | 6 | 8 | 8 | 8 | 7 | 8 | 8 | 8 | 6–10 |
| Aspartic acid | 37 | 36 | 35 | 35 | 31 | 29 | 34 | 30 | 34 | 36 | 37 | 29–37 |
| Cystine-½ | 6 | 6 | 6 | 6 | 6 | 6 | 6 | 6 | 4 | 10 | 8 | 4–10 |
| Glutamic acid | 21 | 23 | 22 | 30 | 28 | 30 | 25 | 38 | 29 | 26 | 28 | 21–38 |
| Glycine | 53 | 52 | 52 | 51 | 52 | 53 | 54 | 54 | 53 | 56 | 51 | 51–56 |
| Histidine | 16 | 16 | 14 | 20 | 16 | 15 | 17 | 20 | 15 | 17 | 14 | 14–20 |
| Isoleucine | 18 | 18 | 18 | 14 | 16 | 18 | 16 | 16 | 18 | 15 | 17 | 14–18 |
| Leucine | 17 | 17 | 17 | 18 | 16 | 16 | 19 | 12 | 17 | 15 | 20 | 12–20 |
| Lysine | 22 | 21 | 23 | 26 | 23 | 20 | 21 | 18 | 20 | 21 | 23 | 18–26 |
| Methionine | 2 | 2 | 2 | 2 | 2 | 6 | 3 | 4 | 2 | 3 | 1 | 1–6 |
| Phenylalanine | 8 | 8 | 7 | 9 | 8 | 8 | 9 | 6 | 8 | 8 | 8 | 6–9 |
| Proline | 12 | 13 | 15 | 10 | 10 | 10 | 13 | 10 | 12 | 13 | 12 | 10–15 |
| Serine | 17 | 17 | 14 | 14 | 13 | 20 | 18 | 18 | 18 | 15 | 19 | 13–30 |
| Threonine | 26 | 25 | 20 | 16 | 27 | 20 | 21 | 17 | 17 | 18 | 18 | 16–27 |
| Tryptophan[1] | Nil | Nil | Nil | Nil | Nil | Nil | Nil | Nil | Nil | 1 | 2 | 0–2 |
| Tyrosine[2] | 2 | 2 | 2 | Nil | 4 | 2 | Nil | 2 | Nil | 2 | Nil | 0–4 |
| Valine | 33 | 32 | 31 | 29 | 29 | 34 | 31 | 35 | 32 | 30 | 30 | 29–35 |
| Total | 317 | 315 | 310 | 304 | 307 | 311 | 315 | 315 | 309 | 317 | 318 | 304–318 |

[1]Colorimetric determination
[2]Average of amino acid analysis and spectrophotometric determination.

It can be seen from Table I that orgotein congeners have from 18–26 and usually 20–23 lysine groups, of which all but 1–3 have titrable (with trinitrobenzene sulfonic acid) $\epsilon$-amino groups. The present invention is directed to orgotein derivatives in which at least a portion of the orgotein lysine groups are alkylated.

SUMMARY OF THE INVENTION

In a composition aspect, this invention relates to N-alkylated orgotein.

tent of alkylation can be determined by the decrease in TNBS-reactive amino groups, taking into account that 1–3 of the lysines of the native orgotein protein are not titrable with TNBS. For example, bovine orgotein assays for only 18 of its 20 to 22 lysines. It should also be borne in mind that monoalkylated lysines are still acylatable, so that only extensively alkylated orgoteins show a reduction in acylatable lysine groups.

Di- and trialkylation of the lysine groups can be followed by counting the charge change shown on electrophoresis upon acylation of the alkylated product. For example, orgotein alkylated with dimethyl sulfate at pH 10 showed a charge change of −2 after acylation with acetic anhydride compared to −20 for unalkylated orgotein.

As is known, the electrophoretic mobility of an ion is a function of the electric field strength, net charge of the ion (including bound conterions), and frictional coefficient. See, for example, C. Tanford "Physical Chemistry of Macromolecules" Wiley, New York (1966). Since the frictional coefficient is dependent on molecular size and shape, and on the solution composition, comparisons of different proteins are not too informative. However, by comparing proteins of similar size and shape, in this case orgotein molecules chemically modified with relatively small groups, under identical electrophoresis conditions, the only variable affecting this electrophoretic mobility is net charge.

Comparison of the electrophoretic patterns of a number of chemically modified orgotein molecules is consistent with this conclusion. Native bovine orgotein electrophoreses mainly as one band (band 1), with minor amounts of faster moving bands (bands 2, 3, etc.) equally spaced ahead of the main band, representing orgotein molecules with a higher ratio of —COOH to —NH$_2$ groups than those molecules forming band 1. Treatment of native bovine orgotein with successively higher concentrations of acetic anhydride at pH 7 leads to the formation of a series of successively more anodic (migrating toward the ⊕ electrode) electrophoretic bands as successively more free amino groups of the orgotein molecules are acetylated. Conversely, treatment with dimethyl sulfate gives a series of bands successively more cathodic (displaced from band 1 toward the ⊖ electrode) as successively more free carboxylic acid groups of the orgotein molecule are esterified.

A graph of distance electrophoresed versus band number is relatively linear at low extents of —COOH or —NH$_2$ modification, but curves gradually at higher modification, since there is a limit to how fast even the most highly charged species can move through solution. The faster migrating species are also more sensitive to salt concentration, and are appreciably retarded when salt-containing samples are electrophoresed. Therefore, since extrapolating more than about two band positions is not always precise, accurate charge counting requires that the unknown be co-electrophoresed with a solution which contains all the bands from 1 through the position of interest (e.g., partially acetylated orgotein).

All of the conventional protein modification reactions which have been applied to the orgotein molecule so far have been consistent with this interpretation, viz., the band positions correspond to integral charge changes from the native orgotein molecule. Acetylation, carbamylation, and N-methylthiocarbamylation all give bands 2, 3, 4, 5, etc., indicating that 1, 2, 3 and 4, respectively, free amino groups have been chemically modified. Similarly, succinylation, which changes ~NH$_3$+ groups to

gives bands 3, 5, 7, 9, etc. Esterification with dimethyl sulfate or with ethyl diazoacetate gives bands −1, −2, −3, −4, etc., indicating that 1, 2, 3, and 4, respectively, free carboxylic acid groups have been chemically modified.

Generally speaking, most, e.g., all except 2-4, of the lysines can be alkylated, even with the milder alkylating agents. All but about one of the accessible (TNBS titrable) lysine groups in each of the orgotein peptide sub-units can be polyalkylated using stronger alkylating conditions, e.g., excess dimethyl sulfate 0.04 M carbonate buffer, pH 10.

As would be expected, when less than all of the titrable lysine amino groups are alkylated, the distribution of the alkyl groups on the orgotein molecule probably is random since none of the titrable lysine amino groups appear abnormally readily alkylatable. Because the orgotein molecule is composed of two identical peptide chains, the alkyl groups of a partially alkylated orgotein will be distributed more or less randomly along each peptide sub-unit but more or less evenly between the two chains. Since a single akylating agent is ordinarily employed, the alkyl groups will all be identical. However, it is possible to produce alkylated orgoteins having two or more different alkyl groups in the molecule and even within each chain thereof.

One way of producing a mixed alkyl orgotein is by alkylating in stages with different alkylating agents. For example, a fraction of the titrable lysine ε-amino groups can be alkylated with a moderate concentration of one alkylating agent, e.g., iodoacetamide, and the remainder of the reactive amino groups alkylated with a high concentration of still another alkylating agent, e.g., dimethyl sulfate. What constitutes a low, or high, concentration of alkylating agent will depend on the relative rates of reaction with protein amino groups and with solvent and will thus depend on the reaction pH and on the alkylating agent, and to a lesser extent on buffer and temperature.

Another method of producing a mixed alkylated orgotein is by hybridization. The term hybridization of orgotein refers to the formation of a mixed orgotein from the peptide chains of two different orgotein molecules, e.g., A$_2$ and B$_2$, A and B being their respective peptide chains. (A$_2$ + B$_2$ ⇌ 2AB). The charge of the heterodimer, AB, on electrophoresis should be the average of that of the homodimers A$_2$ and B$_2$, assuming that the same portion of each sub-init is involved in the binding in all cases.

ε-N-methyl orgotein, produced by alkylating the native orgotein molecule in 0.04 M pH 10 carbonate buffer with excess dimethyl sulfate, and ε-N-ethyl orgotein, produced by alkylating orgotein in the same manner with diethyl sulfate, can each be hybridized with native orgotein or with each other by heating together at 50° C. for 4 hours.

As will be apparent, these hybrid semi-alkylated orgotein molecules can be further alkylated with a different alkylating agent to produce a hybrid alkylated orgotein in which the alkyl groups in one peptide chain differ from those in the other.

The ε-N-alkyl orgoteins of this invention appear to have essentially the same spacial conformation as the native orgotein molecule. Chelated Cu++ and Zn++ contents (Gram Atoms Per Mole) are about the same as that of orgotein. Like orgotein, they are highly resistant to Pronase and other proteolytic enzymatic degradation. Superoxide dismutase (SOD) enzymatic activity is retained.

Although the predominant structural modification of the native orgotein molecule which occurs upon alkylation thereof at alkaline pH is the mono-, di- and, to a lesser extent, trialkylation of the ε-amino groups of the lysines thereof, the free amino groups of the arginine residues thereof and the free carboxylic acid groups of the aspartic acid and glutamic acid groups thereof, as well as other alkylatable groups present in the molecule, especially —OH, and imidazole nitrogen, and possibly also guanidino nitrogen, —SH, —SCH₃, can also be concurrently alkylated, depending on the conditions employed and the reactivity of the alkylating agent. For example, whereas at pH 10 with iodoacetamide, alkylation appears to be solely ε-N-alkylation, alkylation with dimethyl sulfate at pH 10 is less selective and concurrently introduces methyl groups elsewhere in the molecule. Such concomittantly alkylated orgoteins having ε-N-alkyl groups are included in the novel compounds of this invention.

The course of the alkylation, insofar as it involves —COOH alkylation, can be followed directly by a change in overall electrophoretic charge and in the appearance of new bands on electrophoresis. Similarly, N-alkylation, insofar as it renders an otherwise acylatable —NH₂ group resistant to acylation, can be followed by a reduction in the number of acylatable amino groups, compared to the native orgotein molecule.

The exact nature of the N-alkyl groups, like the number of N-alkyl groups, is not critical as long as the alkyl radical is physiologically acceptable. Because of the higher molecular weight of the orgotein molecule, even when the orgotein molecule is fully alkylated with alkyl groups of moderate molecular weight, e.g., $\leq$ 100, the impact on the overall chemical composition is relatively small, i.e., less than 10%. Alkylation also has no apparent significant effect upon the compact spacial conformation of the molecule and resultant stability, e.g., to heating for one hour at 60° C. and to attack by proteolytic enzymes.

As will be apparent, the alkyl group also must be one derived from an alkylating agent capable of alkylating an amino group in water or buffer solution, since the reaction is usually conducted therein. Such alkylating agents include diprimary alkyl sulfates: $(RO)_2SO_2$ (R = $CH_3$, $CH_2H_5$, n-$C_3H_7$, n-$C_4H_9$
activated alkyl halides: $ICH_2COX$ (X = OH, $NH_2$) benzyl and allyl bromides;
activated vinyl groups: $CH_2=CHX$ (X = CN, $SOCH_3$, $SOC_2H_5$, $COCH_3$);
reductive alkylating agents: $RCOR' + BH_4^-$ or $BH_3CN^-$ (R,R' = H, $CH_3$, $C_2H_5$, $C_6H_5$).

Preferred alkyl orgoteins are those wherein the alkyl group is unsubstituted alkyl of 1-4 carbon atoms, e.g., methyl, ethyl, propyl, isopropyl, butyl.

For a method of reductive alkylation of proteins with aromatic aldehydes and sodium cyanoborohydride, see Friedman, M. et al., Int. J. Peptide Protein Res., 6, 1974, 183-185. alkylation with acrylonitrile, see Means & Feeney, "Chemical Modifications of Proteins" Chapter 6, pages 114-117; Fletcher, J. C., Biochem J. 98 34C (1966); Friedman, M. et al., J. Amer. Chem. Soc. 87, 3672 (1965); Friedman, M. et al., J. Org. Chem, 31, 2888 (1966).

Since the exact chemical nature of the alkyl radical is not critical, so long as it is not physiologically toxic in the orgotein molecule and can be formed on the lysine ε-amino groups, contemplated equivalents of the preferred hydrocarbon alkyl groups described above, insofar as they can be formed, are cyclopentyl, cyclohexyl, menthyl, and like cycloalkyl, cyclohexylmethyl, β-cyclopentylpropyl, and like cycloalkylalkyl, benzyl, p-xylyl and phenethyl and like aralkyl. Also contemplated as equivalents are alkyl of 1-8, preferably 1-4, and most preferably methyl or ethyl bearing one or more, preferably one, simple substituents, e.g., carboxy, cyano, carbalkoxy, and amido, e.g., carboxymethyl, cyanomethyl, carbethoxymethyl, carbomethoxymethyl and like carbo-lower-alkoxymethyl, carbamylmethyl, and the corresponding substituted ethyl groups, e.g., —$CH_2CH_2COOH$, —$CH_2CH_2C|N$, —$CH_2CH_2CONH_2$ and —$CH_2CH_2COOR$, wherein R is, e.g., methyl or ethyl, —$CH_2CH_2SOCH_3$, —$CH_2CH_2SOC_2H_5$ and —$CH_2CH_2COCH_3$.

Thus, the alkylated orgoteins of this invention are orgotein congeners including bovine, sheep, horse, pork, dog, rabbit, guinea pig, chicken and human, at least one, e.g., 1,2,3,4,5 and up to all (about 18-26) of whose titratable amino groups are alkylated, i.e., bearing an unsubstituted or substituted alkyl group. In the preferred embodiment, the alkylated amino groups are those of the formula —NH—$CH_2$—R 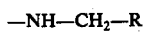

wherein R is H, $CH_3$, $C_2H_5$, n—$C_3H_7$, iso—$C_3H_7$, or other alkyl of up to 7 carbon atoms, —COOH, —COO—LA, —CONH—LA, —CON(LA)₂, —C|N, —$CH_2$—C|N, —Ph, —COPh, —$CH_2OH$ or —$CH(CH_3)OH$, in which LA is lower alkyl of 1-4 carbon atoms and pH is unsubstituted phenyl or phenyl bearing 1-3 simple substituents, e.g., methyl, chloro, bromo, nitro, amido and methoxy, carbomethoxy or carboethoxy, e.g., p-tolyl, sym.-xylyl, p-amidophenyl, m-chlorophenyl and p-methoxyphenyl. Such orgoteins have the formula $(H_2N)_m$—Org—$(NHCH_2R)_n$ 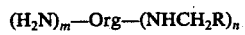

wherein n is an integer from 1 to about 26, preferably at least 10, more preferably about 10-18, and the sum of m and n is the total number of titratable free amino groups in the unmodified congener and R has the values given above, preferably H or LA, e.g., methyl or ethyl, and "Org" is the remainder of the orgotein molecule.

Some of the alkylating agents employed in the process of this invention will simultaneously alkylate some of the free acid groups of the orgotein molecule. These alkylated orgoteins can be represented by the formula

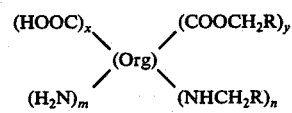

wherein "Org", R, m and n have the values given above, y is the number of alkylated free carboxylic acid groups, e.g., from one up to about 8, preferably 2-6, and x is the remainder of free carboxylic acid groups in the orgotein molecule.

Reagents useful for introducing carboxymethyl and carbamylmethyl groups, respectively, are iodoacetic acid and iodoacetamide. Iodoacetic acid can form stable products with cysteine (sulfhydryl), lysine (amino), histidine (imidazole nitrogens), and methionine (sulfide sulfur) residues in proteins. Since carboxymethylation of any of these groups except methionine increases the net negative charge into the orgotein protein at pH 8.4, electrophoresis can quantitate the total reaction (except carboxymethylation of methionine and carboxymethylation of the second imidazole nitrogen).

In native orgotein, iodoacetic acid and iodoacetamide react predominantly, if not exclusively, with lysine amino groups. Although free thiols react with iodoacetic acid several orders of magnitude faster than do amines, the first few groups in orgotein which are carboxymethylated do not react appreciably faster than do the next 10–20 groups. This is consistent with the reaction of p-mercuribenzoate with orgotein sulfhydryls: there is no reaction with holo-protein. Even with apo-protein, which gives a p-mercuribenzoatesulfhydryl reaction (although slowly under non-denaturing conditions), iodoacetic acid in 10-fold molar excess at pH 7 gave no decrease after several weeks at 4° C. in the sulfhydryl content (determined spectrophotometrically by p-mercuribenzoate titration). The pH dependence of the carboxymethylation reaction as shown by electrophoresis is consistent with reaction of lysine (pK>8) and not of histidine (pK<6), since the extent of reaction at identical initial concentrations increases steadily as the pH approaches 9, with no appreciable reaction at or below neutrality where histidine should still be un-protonated and reactive. On the other hand, ethylchloroformate titration for histidine showed only 5 histidines in carboxymethylated orgotein under conditions which showed 16 in native orgotein.

Evidence that neither methionine nor histidine are available for reaction in native bovine orgotein was provided by an experiment in which orgotein was incubated with 0.2 M iodoacetamide in pH 6.5 0.5 M phosphate buffer for 48 hours. Alkylation of methionine or double alkylation of histidine should have given a more positively charged protein at pH 8.4, but electrophoresis showed no change in SOD activity or band pattern.

The lysine amino groups in orgotein definitely react with iodoacetate, however, The extensively carboxymethylated orgotein migrates on electrophoresis similarly to acetylated orgotein, but has lower SOD activity (about 20% of the unmodified orgotein protein).

In addition to the N-methyl "bovine" orgoteins and orgoteins of the examples hereinafter, other examples of N-alkyl bovine orgoteins of this invention are N-ethyl orgotein, N-propyl orgotein and N-benzyl orgotein, wherein in each instance there are 9 such alkyl groups in each of the two sub-units of the orgotein molecule and the corresponding orgoteins wherein there are an average of 1, 6 or 10 such alkyl groups in each such sub-unit, respectively, and the corresponding human, sheep, horse, pork, dog, rabbit, guinea pig and chicken congeners of each of these.

The alkylated orgotein can be isolated from the reaction solution, preferably after dialysis to remove extraneous ions, by conventional lyophilization, e.g., in the manner described in U.S. Pat. No. 3,758,682. If desired or necessary, the alkylated orgotein can first be purified by ion exchange resin chromatography, electrophoresis and/or gel filtration employing a polymer which acts as a molecular sieve.

Filtration through a micropore filter, e.g., "Millipore", in a conventional manner into sterile vials, optionally after adjusting ionic strength with NaCl and/or sodium phosphate, e.g., to isotonicity, will provide a sterile solution suitable for administration by injection.

The pharmaceutical compositions of this invention comprise an N-alkyl orgotein of this invention and a pharmaceutically acceptable carrier. The form and character which this carrier takes is, of course, dictated by the mode of adminitration.

The pharmaceutical composition preferably is in the form of a sterile injection preparation, for example, as a sterile injectable aqueous solution. The solution can be formulated according to the known art using those carriers mentioned above. The sterile injectable preparation can also be a sterile injectable solution or suspension in a non-toxic parenterally acceptable diluent or solvent, e.g., 1,3-butanediol.

The compositions of this invention combine an effective unit dosage amount of N-alkyl orgotein, i.e., the N-alkyl orgotein is present at a concentration effective to evoke the desired response when a unit dose of the composition is administered by the route appropriate for the particular pharmaceutical carrier. For example, liquid compositions, both topical and injectable, usually contain about 0.5 to 20 mg. of N-alkyl orgotein per 0.25 to 10 cc., preferably about 0.5 to 5 cc., except I.V. infusion solutions, which can also be more dilute, e.g., 0.5 to 20 mg. N-alkyl orgotein per 50–1,000 ml., preferably 100–500 ml. of infusion solution. Tablets, capsules and suppositories usually contain 0.1 to 25 mg., preferably 1 to 10 mg., of N-alkyl orgotein per unit.

N-alkyl orgotein usually is administered by instillation or by injection, e.g., intramuscularly, subcutaneously, intravenously or intradermally. I.M. is preferred, except in case of shock, where I.V. is sometimes preferred for more rapid onset of effect, and in certain localized disorders e.g., radiation and intersititial cystitis, where local injection is often more effective. Individual doses usually fall within the range of 0.5 to 20 mg. The preferred range for humans is about 0.5 to 8 mg.: for horses, about 5.0–10.0 mg. The exact dosage is not critical and depends on the type and the severity of the disease.

N-alkyl orgotein, like orgotein, is effective in treating a wide variety of inflammatory conditions, including those in which synthetic anti-inflammatory agents have limited utility, e.g., because of toxic side effects upon prolonged use.

More specifically, N-alkyl orgotein is efficacious in ameliorating inflammatory conditions and mitigating the effects thereof, for instance those involving the urinary tract and the joints, in various mammals. It is useful in alleviating the symptoms of and the structural deformities associated with posttraumatic arthritis, and rheumatoid diseases, such as bursitis, tendonitis, osteoarthritis.

For further details relating to how to isolate the starting orgotein congeners and how to use the N-alkyl orgotein of this invention, including modes of administration, dosage forms, dosage regimen and inflammatory and other conditions susceptible to treatment with N-alkyl orgotein, see U.S. Pat. No. 3,758,682, whose disclosure is incorporated by reference.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

A solution of 5 mg. bovine orgotein in 4 ml. of 0.04 M carbonate buffer was treated with 20µl dimethyl sulfate and the pH kept at 10.0 by addition of 0.5 M NaOH.

The uptake of base had a half-time of about 37 minutes. Electrophoresis showed SOD-active bands 1 through −5 (average −3). After dialysis, lyophilization and re-solution in 1 ml. water, the protein still had its SOD activity and Cu++ and Zn++ content unchanged from the untreated orgotein. Acetylation of an 85 μg./ml. solution of the modified protein with a total of 3 μl acetic anhydride in 0.4 ml. borate buffer at pH 9 gave an average electrophoretic charge change of only about −2, compared to −20 for native orgotein in the same solution. The pH 10 dimethyl sulfate-treated orgotein is therefore extensively N-methylated i.e., about 18 per molecule.

EXAMPLE 2

Follow the procedure of Example 1, employing, respectively, the corresponding human, sheep, horse, pig, dog, rabbit, guinea pig and chicken orgotein congeners as starting materials. In each case, all except about one lysine of each sub-unit of the orgotein molecule is alkylated.

EXAMPLE 3

Follow the procedure of Example 1, employing diethyl sulfate instead of dimethyl sulfate. The properties of the resulting ε-N-ethylated orgotein are essentially the same as the ε-N-methylated orgotein.

EXAMPLE 4

The ε-amino groups of the lysine residues of bovine orgotein were carboxymethylated with 0.2 M sodium iodoacetate at ambient temperature under the conditions and with the results set forth below.

| Reaction Buffer | Charge Change on Electrophoresis, average ± range |
|---|---|
| orgotein (1.4 mg./ml.) + ICH$_2$CO$_2$−Na+ (0.2 M) | |
| (a) o.3 M pH 3.8 acetate | (only changes are those due to low pH) |
| (b) 0.4 M pH 5.0 acetate | no change up to 72 hours |
| (c) 0.23 M pH 9.2 carbonate | 0 (15 min), 3±2 (2½ hrs.), 5±3 (6½ hrs.) > 18 (72 hrs.) |

From these electrophoretic patterns, it appears that no N-alkylation occurred at pH 3.8 and 5.0 and that at pH 9.2 an average of about 3 —CH$_2$COO$^-$ groups were introduced in 2½ hours; about 5 such groups were introduced in 6½ hours; and about 18 such groups were introduced in 72 hours on the ε-amino nitrogen atoms.

| orgotein (2.8 mg./ml.) + ICH$_2$CO$_2$−Na+ (0.43 M) | |
|---|---|
| (d) pH 6.0 | 0.4 after 5 days at room temperature |
| (e) pH 7.0 | 0.6 (1 day), 1.0 (2 days), 1.5 (5 days) |
| (f) pH 10 | 0 (10 min.), > 3 (2½ hrs.), > 10 (6½ hrs.) |

From the electrophoretic patterns of the thus-treated orgotein it appears that at pH 6 less than half the orgotein molecules were alkylated; at pH 7, in 2 days the orgotein molecules had an average of one ε-amino group alkylated with a —CH$_2$COO$^-$ group and in 5 days an average of two such groups per molecule were introduced. At pH 10, an average of more than three such groups were introduced by 2½ hours and by 6½ hours an average of more than 10 such groups per molecule were introduced.

The products of all the above alkylations in which —CH$_2$COO$^-$ groups were introduced were a mixture of ε-amino alkylated orgoteins containing varying numbers of such groups as evidenced by the appearance of a plurality of bands with varying electrophoretic mobilities.

The preceding examples can be repeated with similar success by substituting the generically or specifically described reactants and/or operating conditions of this invention for those used in the preceding examples.

From the foregoing decription, one skilled in the art can easily ascertain the essential characteristics of this invention, and without departing from the spirit and scope thereof, can make various changes and modifications of the invention to adapt it to various usages and conditions.

What is claimed is:

1. Alkylated orgotein wherein an alkyl group of up to 8 carbon atoms is present on at least one lysine ε-amino group thereof.

2. The alkylated orgotein of claim 1, wherein the orgotein is bovine.

3. The alkylated orgotein of claim 1, having at least 10 alkylated ε-amino groups per molecule.

4. The alkylated orgotein of claim 1, having at least 18 alkylated ε-amino groups per molecule.

5. The alkylated orgotein of claim 3, wherein the orgotein is bovine.

6. The alkylated orgotein of claim 1, wherein the alkylating group is alkyl of 1–4 carbon atoms.

7. The alkylated orgotein of claim 1, wherein the alkylating group is methyl.

8. The alkylated orgotein of claim 6, wherein the orgotein is bovine.

9. The alkylated orgotein of claim 6, having at least 10 alkylated ε-amino groups per molecule.

10. The alkylated orgotein of claim 6, having at least 18 alkylated ε-amino groups per molecule.

11. The alkylated orgotein of claim 8, wherein the alkyl group is methyl.

12. The alkylated orgotein of claim 11, having at least 10 alkylated ε-amino groups per molecule.

13. The alkylated orgotein of claim 11, having at least 18 alkylated ε-amino groups per molecule.

14. A pharmaceutical composition having antiinflammatory activity comprising, in admixture with a pharmaceutically acceptable carrier, an antiinflammatorily effective unit dosage amount of an alkylated orgotein of claim 1.

15. The pharmaceutical composition according to claim 14 in sterile injectable form.

* * * * *